United States Patent [19]

Holland et al.

[11] 4,350,811
[45] Sep. 21, 1982

[54] CHIRAL SUGAR COMPLEXES

[75] Inventors: David Holland, Frodsham; David J. Milner, Manchester, both of England

[73] Assignee: Imperial Chemical Industries Limited, London, England

[21] Appl. No.: 166,838

[22] Filed: Jul. 8, 1980

[30] Foreign Application Priority Data

Jul. 13, 1979 [GB] United Kingdom ................. 7924518

[51] Int. Cl.$^3$ ..................... C07H 15/12; C07H 17/02; C07H 17/04; C07H 23/00
[52] U.S. Cl. ........................................ 536/18; 536/4; 536/121; 536/53; 536/54; 536/55
[58] Field of Search ....................... 536/121, 4, 18, 55, 536/53, 54

[56] References Cited

U.S. PATENT DOCUMENTS

| | | | |
|---|---|---|---|
| 3,868,401 | 2/1975 | Aratani | 260/468 H |
| 4,029,683 | 6/1977 | Aratani | 260/438.1 |
| 4,029,690 | 6/1977 | Aratani | 260/468 H |
| 4,225,592 | 9/1980 | La Katos et al. | 536/121 X |

FOREIGN PATENT DOCUMENTS

| | | |
|---|---|---|
| 50-160241 | 12/1975 | Japan . |
| 1455189 | 11/1976 | United Kingdom . |
| 1459285 | 12/1976 | United Kingdom . |
| 1499094 | 1/1978 | United Kingdom . |

OTHER PUBLICATIONS

Aratani, *Shokubai* (Catalyst), vol. 19, pp. 327–333 (1977).
Adam et al., *J. Chem. Soc. Chem. Comm.* (1979), 234.
Hirai et al., *Agric. Biol. Chem.,* (1976), vol. 40, 169.
Aratani et al., *Tetrahedron Letter,* (1975), 1707.
Aratani et al., *Tetrahedron Letter,* (1977), 2599.
Orioli et al., *J. Amer. Chem. Soc.,* (1966), vol. 88, 277.
MacDonald et al., *Inorganica Chimica Acta,* (1979), vol. 33, L183.
Nakamura et al., *J. Amer. Chem. Soc.,* (1978), 100, 3443, 6544.
Sacconi et al., *J. Chem. Soc.,* (1964), 276.
Nozaki et al., *Tetrahedron,* (1968), 24, 3655.
Zassinovich et al., *J. Organometallic Chem.,* (1977), 133, 377.
Robinson et al., *Inorg. Chem.,* (1963), 2, 1178.
Hubert et al., *Synthesis,* (1976), 9, 600.

*Primary Examiner*—John M. Ford
*Attorney, Agent, or Firm*—Cushman, Darby & Cushman

[57] ABSTRACT

Chiral Schiff bases according to the general formula:

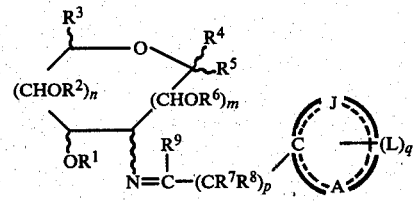

and chiral transition metal complexes thereof, wherein at least the carbon atom of the monosaccharide to which the iminyl nitrogen atom is attached is asymmetric, and at least one of the carbon atoms adjacent the aforesaid carbon atom bears a hydroxyl group, $R^1$ and $R^6$ which may be the same or different, are hydrogen or lower alkyl, $R^2$ is hydrogen, or lower alkyl or together with $R^{10}$ forms a divalent hydrocarbon group, $R^3$ is hydrogen, a sugar residue, or $-CH_2OR^{10}$ in which $R^{10}$ is hydrogen, lower alkyl or together with $R^2$ forms a divalent hydrocarbon group, $R^4$ is hydrogen or $-CH_2OR^{10}$ in which $R^{10}$ is hydrogen, or a lower alkyl, $R^5$ is hydrogen, $OR^1$ or a sugar residue, provided that both $R^4$ and $R^5$ are not hydrogen, $R^7$ and $R^8$ which may be the same or different, are hydrogen, or lower alkyl, or where p is 1, may with the cyclic ring to which $CR^7R^8$ is attached form a fused system, $R^9$ is hydrogen, alkyl, aralkyl, aryl or alkaryl, J is a chain of 3 or 4 atoms which with the group C≡≡≡A forms an aromatic system, which atoms may be carbon atoms or may be a mixture of carbon and one or more hetero atoms which may be the same or different, A is nitrogen, or

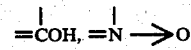

or —NH—, L each of which may be the same or different, represents a substituent attached to a carbon atom in the chain J and is hydrogen, an alkyl group, aralkyl group, aryl, alkaryl or a substituent containing a heteroatom; or two L's together with cyclic group to which they are attached form a fused system, m is 0 or 1, n is 0, 1 or 2, provided that n plus m is 0, 1, 2 or 3, p is 0, 1 or 2 and q is the number of carbon atoms in the chain J. The transistion metal is for example copper (II), chromium (II), manganese (II), iron (II), cobalt (II), nickel (II) or palladium (II). The aforesaid complexes may be used as catalysts in the cyclopropanation of olefins by diazoacetates to form insecticide or insecticide precursors.

9 Claims, No Drawings

CHIRAL SUGAR COMPLEXES

This invention relates to novel chiral Schiff bases, to novel chiral metal complexes, and to the preparation of such bases and complexes; such complexes may be used as catalysts in the preparation of cyclopropane carboxylic acid esters which are compounds useful as insecticides, or insecticide intermediates.

It will be appreciated by those skilled in the art that cyclopropane carboxylic acid esters may, where the cyclopropane ring is appropriately substituted, exist in various geometrical and stereoisomeric forms. In particular, the carbon atom bearing the carboxylic acid group may have the S or R configuration. Moreover, it is known that, where insecticides are derived from cyclopropane carboxylic acids, the isomer having the 1R configuration is insecticidally more effective than its stereoisomer having the 1S configuration.

Cyclopropane carboxylic acid esters which are insecticides or insecticide precursors may be prepared by the reaction of an ester of diazoacetic acid with a carbon-carbon double bond of a suitable monoene or diene. This reaction may be catalysed by various catalysts, e.g. copper bronze, palladium carboxylates, rhodium (II) salts and chiral copper complexes notionally derived from amino acids as disclosed in United Kingdom Pat. No. 1,455,189 and Japanese Patent Kokai No. 160241/75.

We have found that by carrying out the reaction of an appropriate diazoacetic ester with a suitable monoene or diene in the presence of certain novel chiral metal complexes, an enantiomeric excess of cyclopropane carboxylic acid esters having a predetermined configuration is often obtained, and where a monoene is used an excess of the thermodynamically less stable cis isomers is obtained.

In the novel chiral metal complexes the metal is coordinated with a novel chiral Schiff base notionally derived from an amino-monosaccharide and a carbonyl compound containing a cyclic group.

In one aspect therefore the present invention provides chiral Schiff bases according to the general formula:

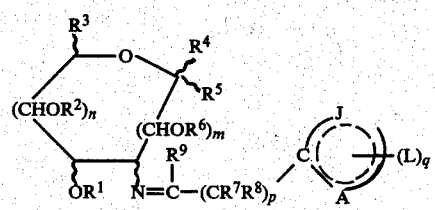

I and chiral transition metal (as hereinafter defined) complexes thereof, wherein at least the carbon atom of the monosaccharide to which the iminyl nitrogen atom is attached is asymmetric, and at least one of the carbon atoms adjacent the aforesaid carbon atom bears a hydroxyl group, $R^1$ and $R^6$ which may be the same or different, are hydrogen or lower alkyl, $R^2$ is hydrogen, or lower alkyl or together with $R^{10}$ forms a divalent hydrocarbon group, $R^3$ is hydrogen, a sugar residue, or —$CH_2OR^{10}$ in which $R^{10}$ is hydrogen, lower alkyl or together with $R^2$ forms a divalent hydrocarbon group, $R^4$ is hydrogen or —$CH_2OR^{10}$ in which $R^{10}$ is hydrogen, or a lower alkyl, $R^5$ is hydrogen, $OR^1$ or a sugar residue, provided that both $R^4$ and $R^5$ are not hydrogen, $R^7$ and $R^8$ which may be the same or different, are hydrogen, or lower alkyl, or where p is 1, may with the cyclic ring to which $CR^7R^8$ is attached form a fused system, $R^9$ is hydrogen, alkyl, aralkyl, aryl or alkaryl, J is a chain of 3 or 4 atoms which with the group C$=\!=\!=$A forms an aromatic system, which atoms may be carbon atoms or may be a mixture of carbon and one or more hetero atoms which may be the same or different, A is nitrogen, or

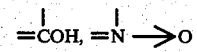

or —NH—, L each of which may be the same or different, represents a substituent attached to a carbon atom in the chain J and is hydrogen, an alkyl group, aralkyl group, aryl, alkaryl or a substituent containing a hetero-atom; or two L's together with the cyclic group to which they are attached form a fused system, m is 0 or 1, n is 0, 1 or 2, provided that n plus m is 0, 1, 2 or 3 p is 0, 1 or 2, and q is the number of carbon atoms in the chain J.

By lower alkyl we mean an alkyl group having up to 5 carbon atoms.

By aromatic system we mean a substantially planar cyclic conjugated system containing $(4z+2)\pi$ electrons, where z is a positive integer.

Specific examples of the chain J are

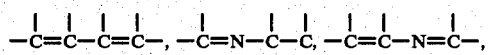

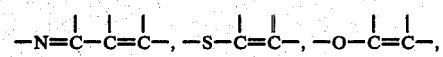

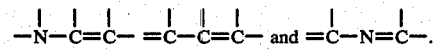

Specific examples of the substituent L containing one or more heteroatoms are OH, $OR^{11}$, $CO_2H$, $CO_2R^{11}$, CN, $CONH_2$, $NH_2$, $NHR^{11}$, $NR_2^{11}$, $NHCOR^{11}$, $NO_2$, SH, $SR^{11}$, $SOR^{11}$, $SO_3H$, $SO_3R^{11}$ or a hydrogen atom, wherein $R^{11}$ is an alkyl, aralkyl or aryl group.

It will be appreciated that the monosaccharide portion of the novel chiral Schiff bases which, in general formula I, are shown in the cyclic hemiacetal or hemiketal form may exist in equilibrium with the corresponding openchain form having a free carbonyl group. Moreover, while the monosaccharide may exist in the furanose form (five membered ring) the pyranose form is usually more stable for the free monosaccharide.

Where $R^2$ and $R^{10}$ together form a divalent hydrocarbyl group the divalent hydrocarbyl group typically is part of a cyclic acetal, e.g. it is methylene, ethylidene or benzylidene; or a cyclic ketal, e.g. isopropylidene; or forms a polyalkylene bridge between oxygen atoms of the monosaccharide e.g. it is ethylene or propylene.

Preferably m is 0, n is 1, $R^1$ is hydrogen, $R^3$ is —$CH_2OR^{10}$, $R^4$ is hydrogen, $R^5$ is lower alkoxy, e.g. methoxy, L is hydrogen, and (a) J is

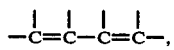

and A is nitrogen or

i.e. the aromatic system in general formula I is 2-pyridyl or 2-hydroxy-phenyl, or (b) J is

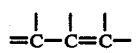

and A is —NH—, i.e. the aromatic system in general formula I is 2-pyrrolyl.

Particularly preferably p is 0, $R^9$ is hydrogen, J is

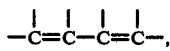

L is hydrogen, q is 4 and A is nitrogen or

More particularly preferably chiral Schiff bases according to the present invention have the general structure represented by the modified Haworth projection formula:

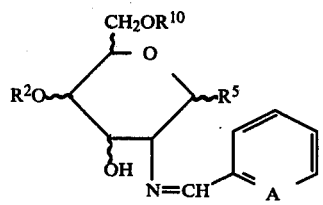

i.e. the configuration of the carbon atom of the monosaccharide to which the iminyl nitrogen atom is attached (C2 of the pyronose ring in formula II) is R, where $R^5$ is lower alkoxy, $R^2$ and $R^{10}$ are both hydrogen or alkyl groups or together form a divalent hydrocarbyl group and A is nitrogen or COH; since we have found that chiral Schiff bases according to the invention in which the pyranose ring has the configuration at C2 (the carbon bonded to the carbon of the acetal or hemiacetal group) specified in general formula II form metal complexes which, when employed as catalysts in the process according to the present invention give preferentially cyclopropane carboxylic acid esters having the 1R configuration.

Examples of specific amino-monosaccharides from which, or from derivatives of which, novel chiral Schiff bases according to the present invention may be prepared, include inter alia 2-amino-2-deoxy-D-glucose, 2-amino-2-deoxy-D-allose, 2-amino-2-deoxy-D-galactose, 2-amino-2-deoxy-D-altrose, 2-amino-2-deoxy-D-mannose, 2-amino-2-deoxy-D-ribose and 2-amino-2-deoxy-D-xylose.

Examples of specific carbonyl compounds from which novel chiral Schiff bases according to the invention may be prepared include inter alia salicylaldehyde, 2-hydroxy-1-naphthaldehyde, 2-pyridinecarboxaldehyde, 2-pyridinecarboxaldehyde-N-oxide, 2-acetylpyridine, 8-quinolinecarboxaldehyde, pyridoxal, and 2-pyrrolecarboxaldehyde.

It is believed that the chiral transition metal complexes according to the present invention, in which a transition metal is co-ordinated with a chiral Schiff base, have structures represented by the general formulae:

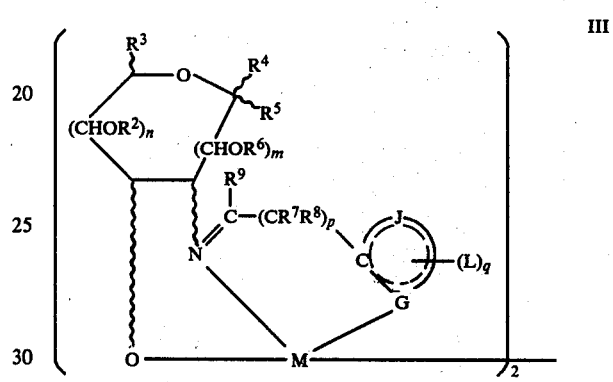

or

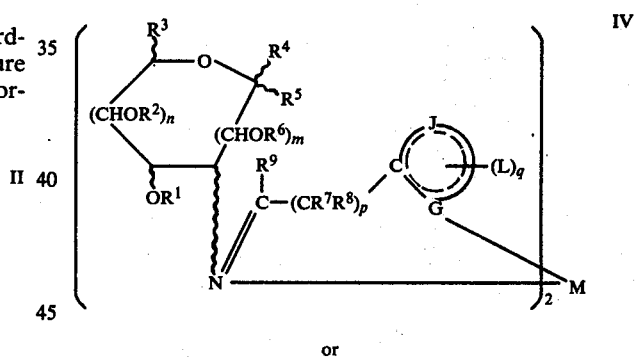

or

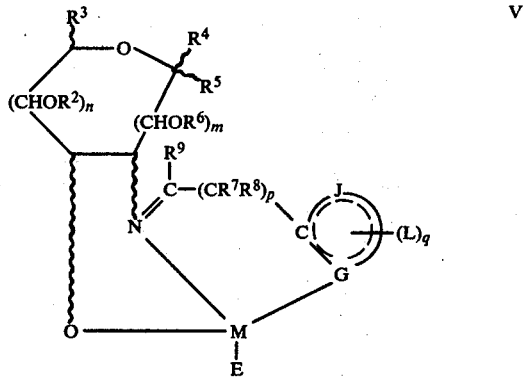

where
$R^{1-9}$, J, L, m, n, p and q have the meanings previously ascribed to them,
E is a monodentate neutral ligand,
G is nitrogen,

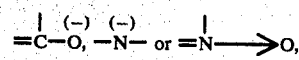

and

M is a metal from the first or second series of the main group of transition metals.

By transition metal we mean a metal which, in any one of its commonly occurring oxidation states, has a partly filled d shell only. In the first series the partly filled d shell is 3d and in the second series the partly filled d shell is 4d.

Preferably the metal is copper (II), chromium (II) manganese (II), iron (II), cobalt (III), nickel (II) or palladium (II). Particularly preferably the metal is copper (II).

It will be appreciated that complexes according to the general formula III are binuclear and compelexes according to the general formulae IV and V are mononuclear and that in the complexes according to the general formulae III and V the Schiff base behaves as a tridentate ligand and that in complexes according to the general formula IV the Schiff base behaves as a bidentate ligand.

Ligands E are suitably Lewis bases, examples are tertiary phosphine oxides and amines such as pyridine.

A preferred group of metal complexes within the invention are those according to general formula IV given above since they give a higher enantiomer excess in the reaction of a monoene or diene with a diazoacetate than given by the metal complexes according to general formulae III and V.

In metal complexes according to the general formulae III, IV or V preferably m is 0 and n is 1, $R^3$ is $CH_2OR^{10}$; $R^4$ is hydrogen; $R^5$ is lower alkoxy, e.g. methoxy; L is hydrogen, and J is

particularly preferably p is 0, $R^9$ is hydrogen,

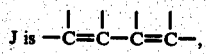

L is hydrogen, q is 4 and G is nitrogen or C—O—; more particularly preferably the metal complex has the general structure represented by the modified Howarth projection formulae:

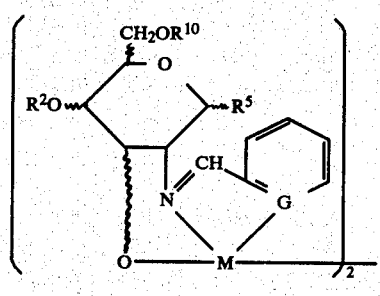

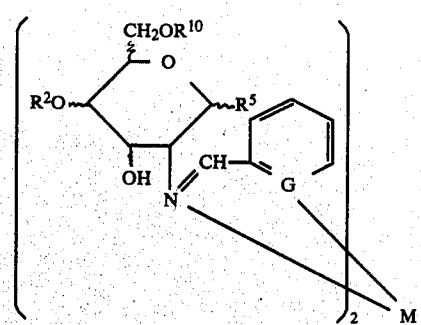

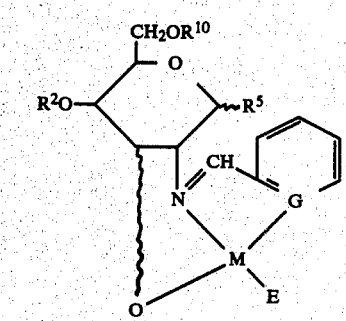

i.e. the configuration of the carbon atoms of the monosaccharide to which the iminyl nitrogen atom is attached (C2 of the pyranose ring in formula VI, VII and VIII) is R, where $R^5$ is lower alkoxy, e.g. methoxy, $R^2$ and $R^{10}$ are hydrogen, or together form a divalent hydrocarbon radical, and G is nitrogen or C—O—.

Where, in the general formulae III-VIII, G is nitrogen or

the metal complex carries a positive charge and an anion is necessary to provide an electrically neutral compound. The anions associated with the metal cation may be inorganic or organic, provided that they are derived from strong acids having a pKa value less than 2.5.

The anions should not be oxidising or reducing agents or otherwise chemically reactive with diazo compounds or other materials used in the preparation of the cyclopropane derivatives. Suitable anions include inter alia halide, fluoroborate, methyl sulphate, bisulphate, aromatic sulphonates, fluorosilicate, sulphate, tetrafluoroborate and tetraphenylborate.

Amino-sugars useful for the preparation of chiral Schiff bases according to the invention may be naturally occurring, e.g. D-glucosamine, or D-mannosamine, or they may be prepared from monosaccharides or from naturally occurring amino-monosaccharides. One known synthetic route to aminosugars is via anhydromonosaccharides as indicated by the following reaction sequence:

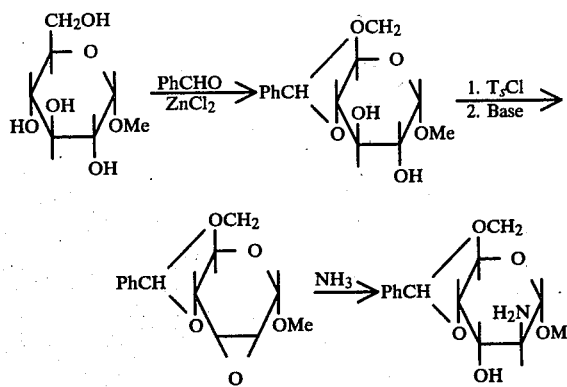

which illustrates the conversion of methyl α-D-glucoside into a derivative of 2-deoxy-2-amino-D-altrose. As examples of other conversions which may be effected by the above reaction sequence we may mention the conversion of D-idose into a derivative of 2-deoxy-2-amino-D-galactose and the conversion of D-arabinose into a derivative of 2-deoxy-2-amino-D-xylose.

Another synthetic route involves the sequence:

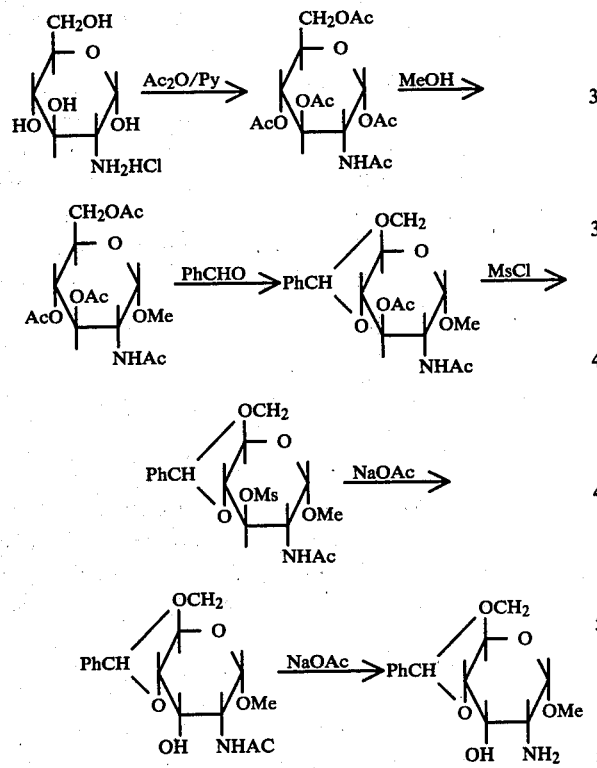

which illustrates the conversion of 2-deoxy-2-amino-D-glucose into a derivative of 2-deoxy-2-amino-D-allose.

The novel chiral Schiff bases according to the invention are prepared by reacting an amino-sugar with a carbonyl compound. The reaction is preferably carried out in the presence of an inert solvent and is often effected near the reflux temperature of the solvent.

Suitable solvents include aromatic hydrocarbons e.g. toluene, alcohols, e.g. methanol and chlorinated hydrocarbons, e.g. 1-2-dichloroethane and chloroform.

Various methods are available for preparing the novel transition metal complexes of chiral Schiff bases according to the present invention. For example, a novel chiral Schiff base may be treated with a transition metal inorganic salt, e.g. copper (II) chloride, to form the corresponding complex, and then, where it is desired to form a fluoroborate, with a suitable fluoroborate, e.g. sodium fluoroborate, to form the corresponding fluoroborate complex (hereinafter Method A). A solution of a chiral primary amino compound may be mixed, e.g. by dropwise addition, to a suspension of a suitable transition metal complex, e.g. bis(salicylaldehydato) copper (II) the reaction mixture stirred, for example for 1 hour, and a novel chiral complex according to the present invention isolated (hereinafter Method B). A solution of a chiral Schiff base according to the present invention, preferably in a suitable solvent, e.g. warm methanol, may be added to a suspension of a suitable transition metal complex, e.g. bis(salicyldehydato) copper (II), in a suitable solvent, e.g. methanol and the resulting mixture stirred to form a novel chiral complex according to the present invention (hereinafter Method C). A chiral Schiff base according to the present invention and a transition metal carboxylate, e.g. copper (II) acetate, preferably dissolved in a suitable solvent, e.g. ethanol, may be heated, preferably under reflux where a suitable solvent is used, for an appropriate time, e.g. 10 minutes; removal of the solvent, where it is used, leaves a binuclear transition metal complex according to the present invention (hereinafter Method D).

Accordingly a further aspect of the present invention provides a method for the preparation of novel chiral metal complexes which method comprises:

(a) reacting a novel chiral Schiff base according to a first aspect of the present invention with a transition metal inorganic salt to form the corresponding transition metal complex and then optionally with a fluoroborate to form the corresponding transition metal fluoroborate complex or, (b) reacting an aminomonosaccharide with a suitable transition metal complex or, (c) reacting a novel chiral Schiff base according to a first aspect of the present invention with a suitable transition metal complex or, (d) reacting a novel chiral Schiff base according to a first aspect of the present invention with a transition metal carboxylate.

The chiral metal complexes according to the present invention may be employed as catalysts in the preparation of cyclopropane carboxylic acid esters of general formula:

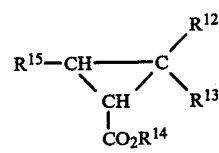  IX by reacting a compound having the general formula:

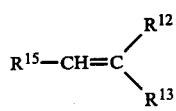  X with an ester of diazoacetic acid.

In the formulae IX and X above:

$R^{12}$ represents a hydrogen atom or a lower alkyl group, $R^{13}$ represents a lower alkyl group, $R^{14}$ represents a lower alkyl group, or a group which forms insecticidally active esters with chrysanthemic acid, e.g. 3-phenyoxybenzyl or α-substituted 3-phenoxybenzyl and, $R^{15}$ represents:

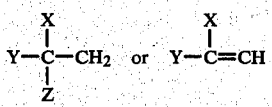

in which Z represents fluorine, chlorine or bromine, X and Y, which may be the same or different, represent fluorine, chlorine, bromine, lower alkyl group, $Q(CF_2)_r$- (in which Q is hydrogen, fluorine or chlorine and r is 1 or 2) or

(where each of U, V, W independently represents an atom of hydrogen, fluorine or chlorine) except that where one of X and Y represents a group of formula $Q(CF_2)_2$- where Q is defined above, the other of X and Y represents an atom of fluorine, chlorine or bromine or a group of formula

where U, V, W are as defined above.

Although the chiral metal complexes according to the present invention may be used as catalysts in the preparation of many of the compounds of formula IX it is particularly useful for the preparation of compounds wherein $R^{12}$ and $R^{13}$ are methyl, $R^{14}$ is ethyl, 3-phenoxybenzyl, α-cyano-3-phenoxybenzyl, or α-ethynyl-3-phenoxybenzyl, and $R^{15}$ is $Cl_2C=CH-$, $CF_3CCl=CH-$, $CF_3CCl_2CH_2-$, $Cl_3C-CH_2-$ or $(CH_3)_2C=CH-$.

The use of the novel chiral complexes of the present invention as catalysts in the reaction of a monoene having a halogenated substituent, or a diene, with a diazoacetate ester to form an insecticide or insecticide intermediate is more fully described in our copending United Kingdom Patent Application Nos. 7,924,521 and 7,924,522 which correspond, respectively, with U.S. applications Ser. Nos. 156,077 and 156,076, both filed June 2, 1980.

Compounds of general formula IX wherein $R^{12}$ and $R^{13}$ represent methyl, $R^{15}$ represents $Cl_2C=CH-$, $R^{14}$ represents 3-phenoxybenzyl or α-cyano-3-phenoxybenzyl are known to be potent isecticides when they have the IR configuration; the isomers having the so-called IR cis configuration being particularly potent and having significantly more insecticidal activity than the isomers having the IR trans configuration. The isomers having the IS configuration have significantly less insecticidal activity. By cis we mean that the hydrogens at C1 and C3 of the cyclopropane ring are in the cis-relationship to one another and by trans we mean that the hydrogens at C1 and C3 of the cyclopropane ring are in the trans-relationship to one another.

The reaction of a compound of general formula X with a diazoacetate is preferably carried out in the presence of an inert solvent in which the cyclopropane product of formula IX is soluble.

Conveniently the solvent used is immiscible with water to facilitate preparation of the diazoacetic ester. More preferably the solvent also has a boiling point lower than that of the monoene or diene of formula X to facilitate recovery of unreacted monoene or diene.

Suitable solvents include saturated chlorinated hydrocarbon solvents, such as ethylene dichloride, dichloromethane, tetrachloroethane, carbon tetrachloride and the like and hydrocarbon solvents such as toluene.

A wide variety of metal complexes according to the present invention may be used as catalyst, the precise 1R:1S ratio of the product being dependent inter alia upon the actual complex used.

The concentration of catalyst in the reaction mixture is not critical, but generally concentrations in the range 0.00001 to 1 g atoms of transition metal per liter of reaction mixture, and especially 0.005 to 1 g atoms, are suitable.

The temperature of the reaction is generally in the range 0° to +130° C., preferably 10° to 90° C.

The diazoacetic acid ester may be prepared by reacting a water soluble acid addition salt (e.g. the hydrochloride) or an ester of glycine with an alkali metal nitrite in an aqueous medium, which is stirred with a water-immiscible solvent into which the diazoacetic acid ester is extracted. Alkali metal nitrites which may be used are, for example, the potassium or sodium salts, and the reaction with the glycine ester is preferably carried out in the presence of an acid catalyst, for example, sulphuric acid.

The solution of diazoacetic acid ester thus formed is then added to a solution of the monoene or diene of formula X maintained at the desired temperature, and containing the catalyst, usually in solution.

The ratio of monoene or diene to diazoacetic ester employed in processes herein disclosed is normally in the range 1:10 to 10:1. It is usual to use enough monoene or diene to react with all the diazoacetate. However, where high conversions of monoene or diene to cyclopropane derivative are desired an excess of diazoacetate may be employed.

Progress of the reaction may be monitored by measuring nitrogen evolution, which may also be used to determine yield of total products, the proportion of the desired product being readily determined by gas liquid chromatography (g.l.c.).

Separation of the desired product from the reaction mixture may be achieved by any convenient means; but it is generally convenient to first distil off the solvent, the monoene or diene, then any esters of maleic and fumaric acids and finally the required product. Alternatively the crude product, where it is a lower alkyl ester, after removal of solvent and unreacted monoene or diene may be used as an intermediate without further purification.

The reaction may also be performed continuously by forming the diazoacetic ester in a first vessel and continuously transferring it, in a solvent, to a second vessel where it is reacted immediately with the monoene or diene, as described and claimed in our British Pat. No. 1,459,285.

It may sometimes be difficult to predict which stereoisomer of a particular amino-sugar constitution (from which the chiral metal complexes according to the present invention are notionally derived) will give an enhanced proportion of the desired optical isomer of the product; but this may be determined experimentally by testing each optical isomer in turn and determining the product distribution, e.g. by glc analysis.

Generally, however, we have found that where chiral metal complexes according to the present invention in which the ring carbon atom bearing the amino group has the same configuration as the ring carbon atom bearing the amino group in 2-deoxy-2-amino-D-glucose, i.e. the aforesaid carbon atom has the R configuration, are used to catalyse the reaction of a diazoacetate with a monoene of formula X an excess of cis cyclopropane isomers over trans cyclopropane isomers is formed, and an excess of 1R enantiomers over 1S enantiomers is formed.

Furthermore, we have found that where chiral transition metal complexes according to the present invention in which the ring carbon atom bearing the amino group has the same configuration as the amino group in 2-deoxy-2-amino-D-glucose are used to catalyse the reaction of a diazoacetate with a diene of formula X an excess of 1R enantiomers over 1S enantiomers is formed, and where chiral transition metal complexes according to the present invention in which the ring carbon atom bearing the amino group has the opposite configuration to that of the ring carbon atom bearing the amino group in 2-deoxy-2-amino-D-glucose are used to catalyse the aforesaid reaction an excess of 1S enantiomers over 1R enantiomers is formed.

Our process may be used to produce a variety of esters of a particular cyclopropane carboxylic acid, the particular ester produced being dependent upon the particular glycine ester used. Thus the process may be used to produce simple alkyl esters, which are useful as intermediates in the preparation of insecticides, or it may be used to produce the insecticides themselves. In the latter case the glycine ester must correspond to the required insecticidal ester. Examples of glycine esters of this type include the ester with 3-phenoxybenzyl alcohol, and with 5-benzyl-3-furyl methanol.

The invention will now be illustrated by the following examples.

EXAMPLE 1

This example illustrates the preparation of a Schiff base from salicylaldehyde and methyl 4,6-O-benzylidene-2-amino-2-deoxy-α-D-altropyranoside. Methyl 4,6-O-benzylidene-2-amino-2-deoxy-α-D-altropyranoside (0.7 g) (prepared by the method of W H Meyer and G H Robertson, J. Amer. Chem. Soc. 1943 65, 8) and salicylaldehyde (0.3 g) in toluene (50 ml) were refluxed for 2 hours. The reaction mixture was cooled and the precipitate filtered off. Recrystallisation from methanol/pet. ether (b.p. 40°–60°) gave the Schiff base derived from salicylaldehyde and methyl 4,6-O-benzylidene-2-amino-2-deoxy-α-D-altropyranoside (m.p. 218° C.).

Elemental analysis for $C_{21}H_{23}O_6N$:

|  | C | H | N |
|---|---|---|---|
| Found: | 65.38 | 5.82 | 3.28 |
| Calculated: | 65.45 | 5.97 | 3.60 |

EXAMPLE 2

By similar procedures to that illustrated in Example 1 other chiral Schiff bases were prepared from methyl 4,6-O-benzylidene-2-amino-2-deoxy-α-D-altropyranoside and the appropriate carbonyl compounds as follows:

(a) The Schiff base derived from 2-hydroxy-1-naphthaldehyde and methyl 4,6-O-benzylidene-2-amino-2-deoxy-α-D-altropyranoside had m.p. of 243° C.

Elemental analysis for $C_{25}H_{25}O_6N$:

|  | C | H | N |
|---|---|---|---|
| Found: | 68.00 | 5.96 | 2.79 |
| Calculated: | 68.97 | 5.75 | 3.22 |

(b) The Schiff base derived from 2-pyridinecarboxaldehyde and methyl 4,6-O-benzylidene-2-amino-2-deoxy-α-D-altropyranoside was prepared from 2-pyridinecarboxaldehyde.

Elemental analysis for $C_{20}H_{22}N_2O_5$:

|  | C | H | N |
|---|---|---|---|
| Found: | 63.82 | 6.07 | 6.96 |
| Calculated: | 64.86 | 5.95 | 7.57 |

EXAMPLE 3

This example illustrates the preparation of chiral Schiff bases derived from methyl 4,6-O-benzylidene-2-amino-2-deoxy-β-D-altropyranoside (prepared by the method of W H Meyer and G J Robertson, J. Amer. Chem. Soc. 1943, 65, 8).

(a) The amino-monosaccharide (0.45 g) and salicylaldehyde (0.2 g) were refluxed in ethanol (30 ml) for 2 hours. The solvent was evaporated off and the residual Schiff base derived from salicylaldehyde and methyl 4,6-O-benzylidene-2-amino-2-deoxy-β-D-altroside had a m.p. of 190°–200° C.

(b) The amino-monosaccharide (0.4 g) and 2-hydroxy-1-naphthaldehyde (0.25 g) were refluxed in ethanol (20 ml) for 2 hours. The solvent was evaporated off and the residual Schiff base derived from 2-hydroxy-1-naphthaldehyde and methyl 4,6-O-benzylidene-2-amino-2-deoxy-β-D-altropyranoside had a m.p. of 115° C.

(c) The amino-monosaccharide (0.5 g) and 2-pyridinecarboxaldehyde (0.2 g) were refluxed in methanol (20 ml) for 2 hours. The solvent was evaporated off and the residual Schiff base derived from 2-pyridinecarboxaldehyde and methyl 4,6-O-benzylidene-2-amino-2-deoxy-β-D-altropyranoside had a m.p. of 248° C.

EXAMPLE 4

This example illustrates the preparation of chiral Schiff bases from methyl 4,6-O-benzylidene-2-amino-2-deoxy-α-D-allopyranoside (prepared by the method of C B Barlow and E A Guthrie, J Chem. Soc., (Part C) 1967, 1196).

(a) The amino-monosaccharide (1.48 g) and salicylaldehyde (0.74 g) were refluxed in toluene (40 ml) for 2½ hours. The solvent was evaporated off at reduced pressure and the residue crystallised to give the Schiff base derived from salicylaldehyde and methyl 4,6-O-benzylidene-2-amino-2-deoxy-α-D-allopyranoside. (1.38 g m.p. 188°–192° C.).

Elemental analysis for $C_{21}H_{23}NO_6$:

|  | C | H | N |
|---|---|---|---|
| Found: | 64.08 | 6.19 | 3.14 |
| Calculated: | 65.45 | 5.97 | 3.64 |

(b) The amino-monosaccharide (0.70 g) and 2-pyridinecarboxaldehyde (0.27 g) were refluxed in toluene (20 ml) for 2½ hours. The solvent was evaporated off at reduced pressure and the residue was dried in vacuo to give the Schiff base derived from 2-pyridinecarboxaldehye and methyl 4,6-O-benzylidene-2-amino-2-deoxy-α-D-allopyranoside as a golden solid (0.68 g m.p. 54°-60° C.).

Elemental analysis for $C_{20}H_{22}N_2O_5$:

|  | C | H | N |
|---|---|---|---|
| Found: | 62.96 | 6.43 | 6.76 |
| Calculated: | 64.86 | 5.94 | 7.57 |

EXAMPLE 5

This example illustrates the preparation of chiral Schiff bases from methyl 2-amino-2-deoxy-β-D-glucopyranoside (prepared by the method of A Neuberger and R P Rivers, J. Chem. Soc., 1939, 122).

(a) The amino-monosaccharide (0.8 g) and salicylaldehyde (0.55 g) were heated at reflux in ethanol (50 ml) for 2 hours. The reaction mixture was evaporated to dryness to leave the Schiff base derived from salicyladehyde and methyl 2-amino-2-deoxy-β-D-glucopyranoside as a yellow oil.

(b) The amino-monosaccharide (0.8 g) and 2-hydroxy-1-naphthaldehyde were heated at reflux in ethanol (50 ml) for 2 hours. The reaction mixture was evaporated to dryness to leave the Schiff base derived from 2-hydroxy-1-naphthaldehyde and methyl 2-amino-2-deoxy-β-D-glucopyranoside as a green oil.

(c) The amino-monosaccharide (0.8 g) and 2-pyridinecarboxaldehyde (0.44 g) were heated at reflux in ethanol (50 ml) for 2 hours. The reaction mixture was evaporated to dryness to leave the Schiff base derived from 2-pyridinecarboxaldehyde and methyl 2-amino-2-deoxy-β-D-glucopyranoside as a yellow solid.

EXAMPLE 6

This example illustrates the preparation of chiral Schiff bases from methyl 2-amino-2-deoxy-α-D-glucopyranoside (prepared by the method of A Neuberger and R. P. Rivers J. Chem. Soc. 1939, 122)

(a) The amino-monosaccharide (0.6 g) and salicylaldehyde (0.38 g) were heated at reflux in ethanol (50 ml) for 2 hours. The reaction mixture was evaporated to dryness to leave the Schiff base derived from salicylaldehyde and methyl 2-amino-2-deoxy-α-D-glucopyranoside as a yellow oil.

(b) The amino-monosaccharide (0.6 g) and 2-pyridinecarboxaldehyde (0.33 g) were heated at reflux in ethanol (50 ml) for 2 hours. The reaction mixture was evaporated to dryness to leave the Schiff base derived from 2-pyridinecarboxaldehyde and 2-amino-2-deoxy-α-D-glucopyranoside as a yellow oil.

EXAMPLE 7

This example illustrates the preparation of metal complexes of Schiff bases derived from methyl 4,6-O-benzylidene-2-amino-2-deoxy-α-D-altropyranoside.

(a) The Schiff base derived from 2-hydroxy-1-naphthaldehyde and methyl 4,6-O-benzylidene-2-amino-2-deoxy-α-D-altropyranoside (0.435 g) was added in portions over 1 hour with stirring to bis(salicylaldehydato) copper (II) (0.153 ) in methanol (10 ml) The reaction mixture was stirred for 3 hours and the mononuclear copper (II) complex of the Schiff base was filtered off as a green solid, m.p. 218° C., $[\alpha]_D = +35°$ (Method C).

Elemental analysis for $C_{50}H_{48}O_{12}N_2Cu$:

|  | C | H | N |
|---|---|---|---|
| Found: | 63.79 | 4.79 | 2.70 |
| Calculated: | 64.27 | 5.36 | 3.00 |

(b) Cupric acetate monohydrate (0.2 g) and the Schiff base derived from 2-hydroxy-1-naphthaldehyde and methyl 4,6-O-benzylidene-2-amino-2-deoxy-α-D-altropyranoside (0.453 g) were heated at reflux in methanol (20 ml) for 30 mins. The binuclear copper (II) complex of the Schiff base was filtered off as a green solid, dec. >250° C. $[\alpha]_D = +200°$ (Method D).

Elemental analysis for $C_{25}H_{23}O_6NCu$:

|  | C | H | N |
|---|---|---|---|
| Found: | 59.80 | 5.25 | 1.90 |
| Calculated: | 60.18 | 5.02 | 2.81 |

(c) Cupric chloride dihydrate (0.170 g) in water (4 ml) was added slowly to the Schiff base derived from 2-pyridinecarboxaldehyde and methyl 4,6-O-benzylidene-2-amino-2-deoxy-α-D-altropyranoside (1.23 g). Water (2 ml) and methanol (6 ml) were added and the mixture was stirred for 30 minutes. Sodium fluoroborate (0.2 g) in water (1 ml) was added and stirring was continued for 10 minutes. The solvent was evaporated off to leave a mononuclear copper (II) complex of the Schiff base as a green residue m.p. 170° C. (Method A).

(d) The Schiff base derived from salicylaldehyde and methyl 4,6-O-benzylidene-2-amino-2-deoxy-α-D-altropyranoside (0.385 g) was added in portions with stirring over 1 hour to bis(salicylaldehydato) copper (II) (prepared by reacting cupric chloride and sodium salicylaldehydate in water, extracting into toluene and evaporating) (0.153 g) in methanol (10 ml). The reaction mixture was stirred for 1 hour and a solid was filtered off. Evaporation of the filtrate left a green mononuclear copper (II) complex of the Schiff base m.p. 190°-205° C.$[\alpha]_D = +300°$ (Method C).

Elemental analysis for $C_{42}H_{44}N_2O_{12}Cu$:

|  | C | H | N |
|---|---|---|---|
| Found: | 62.90 | 5.33 | 2.81 |
| Calculated: | 60.60 | 5.33 | 3.37 |

(e) Methyl 4,6-O-benzylidene-2-amino-2-deoxy-α-D-altropyranoside (0.56 g) in methanol (10 ml) was added dropwise with stirring to a suspension of bis (salicylaldehydato) copper (II) (0.154 g) in methanol (5 ml). The reaction mixture was stirred for 3 hours and then filtered (Method B).

(f) Cupric acetate monohydrate (0.2 g) and the Schiff base derived from salicylaldehyde and methyl 4,6-O-benzylidene-2-amino-2-deoxy-α-D-altropyranoside (0.385 g) were heated under reflux in methanol (10 ml) for 10 minutes. The methanol was evaporated off and the residue was extracted with toluene. The toluene extract was washed with a saturated aqueous sodium bicarbonate solution, then with water, dried and the toluene evaporated off to leave a green binuclear copper (II) complex of the Schiff base. m.p. 188° C. $[\alpha]_D +530°$ (Method A).

Elemental analysis for $C_{21}H_{21}NO_6Cu$:

|  | C | H | N |
|---|---|---|---|
| Found: | 52.00 | 5.32 | 2.20 |
| Calculated: | 56.43 | 4.74 | 3.13 |

EXAMPLE 8

This example illustrates the preparation of metal complexes of Schiff bases derived from methyl 4,6-O-benzylidene-2-amino-2-deoxy-β-D-altropyranoside.

(a) The Schiff base derived from salicylaldehyde and methyl 4,6-O-benzylidene-2-amino-2-deoxy-β-D-altropyranoside (0.35 ) was added in portions over 1 hour with stirring to bis(salicylaldehydato) copper (II) (0.14 g) (prepared as in Example 7) in methanol (10 ml) at 20° C. The reaction mixture was stirred for 2 hours and a solid was filtered off. The filtrate was evaporated to dryness to leave a copper (II) complex of the Schiff base (Method C).

(b) The Schiff base derived from 2-hydroxy-1-naphthaldehyde and methyl 4,6-O-benzylidene-2-amino-2-deoxy-β-D-altropyranoside (0.5 g) and bis(salicylaldehydato) copper (II) were reacted as above to give a copper (II) complex of the Schiff base (Method C).

(c) Cupric chloride dihydrate (0.069 g) in water (2 ml) was added slowly with stirring to the Schiff base derived from 2-pyridinecarboxaldehyde and methyl 4,6-O-benzylidene-2-amino-2-deoxy-β-D-altropyranoside (0.5 g) in methanol (10 ml). The reaction mixture was stirred for 1 hour, sodium fluoroborate (0.17 g) was added and stirring continued for a further 30 minutes. The solvent was removed (Method A).

EXAMPLE 9

This example illustrates the preparation of metal complexes of Schiff bases derived from methyl 4,6-O-benzylidene-2-amino-2-deoxy-α-D-allopyranoside.

(a) Cupric acetate monohydrate (0.24 g) and the Schiff base derived from salicylaldehyde and methyl 4,6-O-benzylidene-2-amino-2-deoxy-α-D-allopyranoside (0.65 g) were heated at reflux in ethanol (10 ml) for 10 minutes. The ethanol was evaporated off and the residue was dissolved in toluene. The toluene solution was washed with saturated aqueous sodium bicarbonate solution, then water, dried and evaporated. The residue was washed with methanol and dried to give a binuclear copper (II) complex of the Schiff base (0.3 g) as a deep green solid m.p. 194°-197° C. (Method D).

Elemental analysis for $C_{21}H_{21}NO_6Cu$:

|  | C | H | N | Cu |
|---|---|---|---|---|
| Found: | 56.15 | 5.05 | 2.63 | 13.6 |
| Calculated: | 56.43 | 4.74 | 3.13 | 14.2 |

(b) Methyl 4,6-O-benzylidene-2-amino-2-deoxy-α-D-allopyranoside (0.7 g) in methanol (10 ml) was added dropwise with stirring over 1 hour to a suspension of bis(salicylaldehydato) copper (II) (0.38 g) in methanol (10 ml). The reaction mixture was stirred for 1 hour and a solid was filtered off. The filtrate was evaporated to dryness to leave a mononuclear copper (II) complex of the Schiff base as a green solid (0.5 g) (Method B). m.p. 150°-152° C.

Elemental analysis for $C_{42}H_{44}N_2O_{12}Cu$:

|  | C | H | N | Cu |
|---|---|---|---|---|
| Found: | 61.77 | 5.40 | 2.91 | 7.4 |
| Calculated: | 60.60 | 5.69 | 3.37 | 7.6 |

EXAMPLE 10

This example illustrates the preparation of metal complexes of Schiff bases derived from methyl 2-amino-2-deoxy-β-D-glucopyranoside.

(a) Bis(salicylaldehydato) copper (II) (0.4 g) and the Schiff base derived from salicylaldehyde and methyl 2-amino-2-deoxy-β-D-glucopyranoside (1.15 g) was stirred in methanol (10 ml) for 2 hours. The reaction mixture was evaporated to dryness to leave a mononuclear copper (II) complex of the Schiff base (Method C).

(b) Bis(salicylaldehydato) copper (II) (0.4 g) and the Schiff base derived from 2-hydroxy-1-naphthaldehyde and methyl 2-amino-2-deoxy-β-D-glucopyranoside (1.40 g) were stirred in methanol (10 ml) for 2 hours. The reaction mixture was evaporated to dryness to leave a mononuclear copper (II) complex of the Schiff base (Method C).

(c) Cupric chloride dihydrate (0.17 g) in water (4 ml) was added to the Schiff base derived from 2-pyridinecarboxaldehyde and methyl 2-amino-2-deoxy-β-D-glucopyranoside (1.20 g) in methanol (10 ml). The reaction mixture was stirred for 1 hour, it was then concentrated on rotary evaporator and placed in a refrigerator overnight. The resulting brown solid was filtered off, washed with water and dried to afford the chloride of a mononuclear copper (II) complex of the Schiff base, m.p. 105° C.

Elemental analysis for $C_{26}H_{36}N_4O_{10}CuCl_2$:

|  | C | H | N |
|---|---|---|---|
| Found: | 44.18 | 5.35 | 7.34 |
| Calculated: | 44.67 | 5.15 | 8.02 |

(d) Example 5 (c) was repeated except that sodium fluoroborate (0.4 g) was added after 1 hour and the reaction mixture stirred for a further hour before concentration. The fluoroborate of a mononuclear Schiff base was obtained as a known solid, m.p. 191°-193°.

Elemental analysis for $C_{26}H_{36}N_4O_2CuB_2F_8$:

|  | C | H | N |
|---|---|---|---|
| Found: | 38.79 | 4.60 | 5.52 |
| Calculated: | 38.94 | 4.49 | 6.99 |

EXAMPLE 11

This example illustrates the preparation of metal complexes of Schiff bases derived from methyl 2-amino-2-deoxy-α-D-glucopyranoside.

(a) Bis(Salicylaldehydato) copper (II) (0.3 g) and the Schiff base derived from salicylaldehyde and methyl 2-amino-2-deoxy-α-D-glucopyranoside (0.85 g) were stirred in methanol for 2 hours. The reaction mixture was evaporated to dryness to leave a mononuclear copper (II) complex of the Schiff base (Method B).

(b) Cupric chloride dihydrate (0.12 g) in water (3 ml) was added to the Schiff base derived from 2-pyridinecarboxaldehyde and methyl 2-amino-2-deoxy-α-D-glucopyranoside (0.90 g) in methanol (3 ml). The reaction mixture was stirred for 1 hour, sodium fluoroborate (0.3 g) was added and stirring was continued for a further 2 hours. The reaction mixture was evaporated to dryness to leave a mononuclear copper (II) complex of the Schiff base (Method A).

EXAMPLES 12–16

These examples illustrate the use of the novel metal complexes as catalysts in the reaction of a diazoacetate ester with a halogenated diene of general formula X. 1,1-Dichloro-4-methyl-1,3-pentadiene (DCMP-1,3) (9.1 g) (60 m.mole) was added to a measured quantity of the appropriate catalyst (≡0.04 mg atoms of metal) under an atmosphere of nitrogen. A solution (0.25 ml) containing dodecane (1.76 m.mole per ml) in a chlorinated solvent (1,2 dichloroethane or 1,1,2,2-tetrachloroethane) was added as a glc internal standard. The mixture was then heated to 50° C. with stirring under an atmosphere of nitrogen. A solution containing DCMP-1,3 (60 mmole) and diazoacetic acid ethyl ester (DAE) (15 m.mole) in toluene (2 ml) was then added to the stirred mixture over a period of 20 hours. Nitrogen evolution was monitored throughout the reaction and small samples of the reaction mixture were withdrawn from time to time for glc analysis. % yields were determined in terms of moles of ethyl 2,2-dimethyl-3(2,2-dichlorovinyl)cyclopropanecarboxylate (PAE) per mole of nitrogen evolved (i.e. mole of diazoacetic ester decomposed).

The solvent for the reaction (1,2-dichloroethane) was removed using a rotary evaporator and the PAE isolated by column chromatography using an alumina (type H) column. Unreacted DCMP-1,3 was washed from the column by elution with petroleum ether (40°–60° C.) and the PAE subsequently recovered by elution with diethyl ether. Diethyl fumarate and diethyl maleate co-products remained in the column.

The PAE was hydrolysed with ethanolic NaOH to give the free acid which was treated with thionyl chloride to give the acid chloride. This was reacted with 2-d-octanol to give a mixture of four diastereoisomers. These were analysed by glc on a 15 ft column of 5% LAC-2R-446 on Embacel at 125° C. The results are set out in Table 1 and 2.

From Table 1 it can be seen that an enantiomeric excess of the 1R isomers is obtained when the reaction of 1,1-dichloro-4-methyl-1,3-pentadiene with diazoacetic acid ethyl ester is catalysed by a mononuclear copper (II) complex of a Schiff base having at $C_2$ of the monosaccharide the configuration specified in general formula VI. From Table 2 it can be seen that an enantiomeric excess of the 1S isomers is obtained when the same reaction is catalysed by a mononuclear copper complex of a Schiff base having at C2 of the monosaccharide the configuration opposite to that specified in general formula VI.

TABLE 1

| Ex No | Catalyst | Method of Catalyst Preparation | Yield of PAE[a] (%) | Isomer Ratio (%) |
|---|---|---|---|---|
| 12 | Mononuclear Cu (II) complex of the Schiff base derived from salicylaldehyde and methyl 4,6-O-benzylidene-2-amino-2-deoxy-α-D-allopyranoside | C | 43 | 25 (1R cis)<br>18 (1S cis)<br>32 (1R trans)<br>25 (1S trans) |
| 13 | Mononuclear Cu (II) complex of the Schiff base derived from salicylaldehyde and methyl 4,6-O-benzylidene-2-amino-2-deoxy-α-D-allopyranoside | B | 17 | 24 (1R cis)<br>20 (1S cis)<br>29 (1R trans)<br>27 (1S trans) |
| 14 | Mononuclear Cu (II) complex of the Schiff base derived from 2-pyridine carboxaldehyde and methyl 2-amino-2-deoxy-β-D-glucopyranoside | A | 49 | 19 (1R cis)<br>17 (1S cis)<br>34 (1R trans)<br>30 (1S trans) |
| 15 | Mononuclear Cu (II) complex of the Schiff base derived from salicylaldehyde and methyl 2-amino-2-deoxy-β-D-glucopyranoside | C | 44 | 22 (1R cis)<br>18 (1S cis)<br>29 (1R trans)<br>31 (1S trans) |

[a]based on $N_2$ evolved

TABLE 2

| Ex No | Catalyst | Method of Catalyst Preparation | Yield of PAE[a] (%) | Isomer Ratio (%) |
|---|---|---|---|---|
| 16 | Mononuclear Cu (II) complex of the Schiff base derived from 2-pyridinecarboxaldehyde and methyl 4,6-O-benzylidene-2-amino-2-deoxy-β-D-altropyranoside | A | 14 | 13 (1R cis)<br>27 (1S cis)<br>29 (1R trans)<br>30 (1S trans) |
| 17 | Mononuclear Cu (II) complex of the Schiff base derived from salicylaldehyde and methyl 4,6-O-benzylidene-2-amino-2-deoxy-α-D-altropyranoside | B | 44 | 20 (1R cis)<br>22 (1S cis)<br>27 (1R trans)<br>30 (1S trans) |

TABLE 2-continued

| Ex No | Catalyst | Method of Catalyst Preparation | Yield of PAE[a] (%) | Isomer Ratio (%) |
|---|---|---|---|---|
| 18 | Mononuclear Cu (II) complex of the Schiff base derived from salicylaldehyde and methyl 4,6-O-benzylidene-2-amino-2-deoxy-β-D-altropyranoside | C | 10 | 9 (1R cis)<br>31 (1S cis)<br>31 (1R trans)<br>29 (1S trans) |
| 19 | Mononuclear Cu (II) complex of the Schiff base derived from 2-pyridinecarboxaldehyde and methyl 4,6-O-benzylidene-2-amino-2-deoxy-α-D-altropyranoside | A | 22 | 21 (1R cis)<br>19 (1S cis)<br>25 (1R trans)<br>35 (1S trans) |

[a]based on $N_2$ evolved

EXAMPLES 20-25

This example illustrates the use of the novel metal complexes as catalysts in the reaction of a diazoacetic ester with a halogenated monoene of general formula X.

In Examples 20-24, 2,2-dichloro-5-methyl-1,1,1-trifluorohex-4-ene (30 m mole) and in Example 25, 1,1,1-trichloro-4-methyl-3-pentene (30 m mole) and a copper (II) complex of a novel Schiff base (equivalent to 2 mg atoms of copper) were treated with a toluene solution of ethyl diazoacetate (containing 0.7 m mole of diazoacetate per ml of solution) at 80° C. Nitrogen (6.9 m mole) was evolved, and the solutions were found to contain ethyl 3-(2',2'-dichloro-3',3',3'-trifluoropropyl)-2,2-dimethylcyclopropane-1-carboxylate and ethyl 3(2',2',2'-trichloroethyl)-2,2-dimethylcyclopropane-1-carboxylate.

The isomer ratios were determined by glc of the 2-d-octyl esters. The results are given in Table 3 from which it can be seen that an enantiomeric excess of the 1R isomers is obtained when the reaction of (a) 2,2-dichloro-5-methyl-1,1,1-trifluorohex-4-ene and (b) 1,1,1-trichloro-4-methyl-3-pentene with diazoacetic acid ethyl ester is catalysed by a copper (II) complex of a Schiff base having at C2 of the monosaccharide the configuration specified in general formula VI.

metals in co-ordination with a chiral Schiff base of the formula:

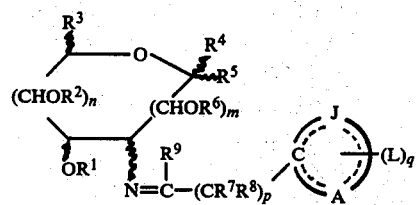

wherein
at least the carbon atom of the monosaccharide to which carbon atom the iminyl nitrogen atom is attached is asymmetric,
at least one of the carbon atoms adjacent the said carbon atom bears a hydroxyl group,
$R^1$ and $R^6$ which may be the same or different, are hydrogen or lower alkyl,
$R^2$ is hydrogen or lower alkyl or where n is 1 and $R^3$ is $-CH_2OR^{10}$, $OR^2$ and $OR^{10}$ together form an acetal or ketal residue,
$R^3$ is $-CH_2OR^{10}$ in which $R^{10}$ is hydrogen, lower alkyl or where n is 1, $OR^2$ and $OR^{10}$ together form an acetal or ketal residue,
$R^4$ is hydrogen or $-CH_2OR^{10}$ in which $R^{10}$ is hydrogen, or a lower alkyl,

TABLE 3

| Ex No | Catalyst | Method of Catalyst Preparation | Yield[a] of cyclopropane (%) | Isomer Ratio (%) |
|---|---|---|---|---|
| 20 | Mononuclear Cu (II) complex of the Schiff base derived from salicylaldehyde and methyl 4,6-O-benzylidene-2-amino-2-deoxy-α-D-allopyranoside | C | 13 | 41 (1R cis)<br>17 (1S cis)<br>20 (1R trans)<br>22 (1S trans) |
| 21 | Mononuclear Cu (II) complex of the Schiff base derived from 2-pyridinecarboxaldehyde and methyl 4,6-O-benzylidene-2-amino-2-deoxy-α-D-allopyranoside | A | 8 | 58 (1R cis)<br>22.5 (1S cis)<br>13.5 (1R trans)<br>6 (1S trans) |
| 22 | Binuclear Cu (II) complex of the Schiff base derived from salicylaldehyde and methyl 4,6-O-benzylidene-2-amino-2-deoxy-α-D-glucopyranoside | D | 23 | 32 (1R cis)<br>22 (1S cis)<br>22 (1R trans)<br>24 (1S trans) |
| 23 | Mononuclear Cu (II) complex of the Schiff base derived from salicylaldehyde and methyl 4,6-O-benzylidene-2-amino-2-deoxy-α-D-glucopyranoside | B | 25 | 30 (1R cis)<br>21 (1S cis)<br>25 (1R trans)<br>24 (1S trans) |
| 24 | Mononuclear Cu (II) complex of the Schiff base derived from salicylaldehyde and methyl 4,6-O-benzylidene-2-amino-2-deoxy-α-D-glucopyranoside | C | 10 | 33 (1R cis)<br>25 (1S cis)<br>18 (1R trans)<br>24 (1S trans) |
| 25 | Mononuclear Cu (II) complex of the Schiff base derived from 2-pyridinecarboxaldehyde and methyl 4,6-O-benzylidene-2-amino-2-deoxy-α-D-allopyranoside | A | 33 | 33 (1R cis)<br>23 (1S cis)<br>25 (1R trans)<br>19 (1S trans) |

[a]based on nitrogen evolved

We claim:
1. A metal complex which comprises a metal from the first or second series of the main group of transition

$R^5$ is hydrogen or $OR^1$ provided that both $R^4$ and $R^5$ are not hydrogen, $R^7$ and $R^8$, which may be the same or different, are hydrogen, or lower alkyl, or where p is 1, may with the cyclic ring to which $CR^7R^8$ is attached form a fused system, $R^9$ is hydrogen, alkyl, aralkyl, aryl or alkaryl, J is a chain of 3 or 4 atoms which chain is chosen from the group consisting of $$-\overset{|}{C}-\overset{|}{C}-\overset{|}{C}=\overset{|}{C}-,\ -\overset{|}{C}=N-\overset{|}{C}=\overset{|}{C}-,\ -\overset{|}{C}=\overset{|}{C}-N\equiv C,$$

$$-N\equiv\overset{|}{C}-\overset{|}{C}=\overset{|}{C}-,\ -S-\overset{|}{C}=\overset{|}{C}-,\ -O-\overset{|}{C}=\overset{|}{C}-,$$

$$-N-\overset{|}{C}=\overset{|}{C}-,\ =\overset{|}{C}-\overset{|}{C}=\overset{|}{C}-,\text{ and }=\overset{|}{C}-N=\overset{|}{C}-$$

and with the group C----A forms a substantially planar cyclic conjugated system containing $(4z+2)\pi$ electrons, where z is a positive integer, A is nitrogen, or $$=\overset{|}{C}OH,\ =\overset{|}{N}\rightarrow O\text{ or }-NH-,$$

L each of which may be the same or different, represents a substituent attached to a carbon atom in the chain J and is (a) hydrogen, alkyl, aralkyl, aryl, alkaryl, hydroxy, $OR^{11}$, $OCOR^{11}$, CHO, $COR^{11}$, $CO_2H$, $CO_2R^{11}$, CN, $CONH_2$, $NH_2$, $NHR^{11}$, $NR^{11}_2$, $NHCOR^{11}$, $NO_2$, SH, $SR^{11}$, $SOR^{11}$, $SO_3R^{11}$ and a halogen atom, where $R^{11}$ is alkyl, aralkyl, or aryl, or (b) where p is 0, the L's on two adjacent atoms in the chain J may, together with the ring

[structure showing -C with ring containing J, A, and (L)_m]

form a fused bicyclic system, m is 0 to 1, n is 0 or 1, provided that n plus m is 0 or 1 p is 0, 1 or 2, and q is the number of carbon atoms in the chain J.

2. A metal complex as claimed in claim 1 wherein m is 0, n is 1, $R^1$, $R^4$ and L are hydrogen, $R^3$ is $CH_2OR^{10}$, $R^5$ is lower alkoxy, and (a) J is $$-\overset{|}{C}=\overset{|}{C}-\overset{|}{C}=\overset{|}{C}-$$

and A is nitrogen or $$=\overset{|}{C}-OH$$

or (b) J is $$=\overset{|}{C}-\overset{|}{C}=\overset{|}{C}-$$

and A is —NH—.

3. A metal complex as claimed in claim 2 wherein p is 0, $R^9$ is hydrogen, J is $$-\overset{|}{C}\equiv\overset{|}{C}-\overset{|}{C}=\overset{|}{C}-$$

and A is nitrogen or $$=\overset{|}{C}-OH.$$

4. A metal complex as claimed in claim 1 in which the asymmetric carbon atom has the R or S configuration.

5. A metal complex as claimed in claim 5 prepared from a Schiff base which has the structure represented by the modified Haworth projection formula:

[Haworth projection structure with $CH_2OR^{10}$, $R^2O$, $R^5$, OH, N=CH, A]

where $R^5$ is lower alkoxy, $R^2$ and $R^{10}$ are both hydrogen or together form a divalent hydrocarbyl group or $R^2$ is lower alkyl and A is nitrogen or COH.

6. A metal complex as claimed in claim 1 in which the transition metal is selected from the group consisting of copper (II), chromium (II), manganese (II), iron (II), cobalt (II), nickel (II), and palladium (II).

7. A metal complex as claimed in claim 6 in which the transition metal is copper (II).

8. A metal complex as claimed in claim 6 which has the structure:

[Complex structure showing ring with $R^3$, O, $R^4$, $R^5$, (CHOR$^2$)$_n$, (CHOR$^6$)$_m$, $R^9$, $C-(CR^7R^8)_p$, N, O, M, G, J, (L)$_q$, with subscript 2]

or

-continued

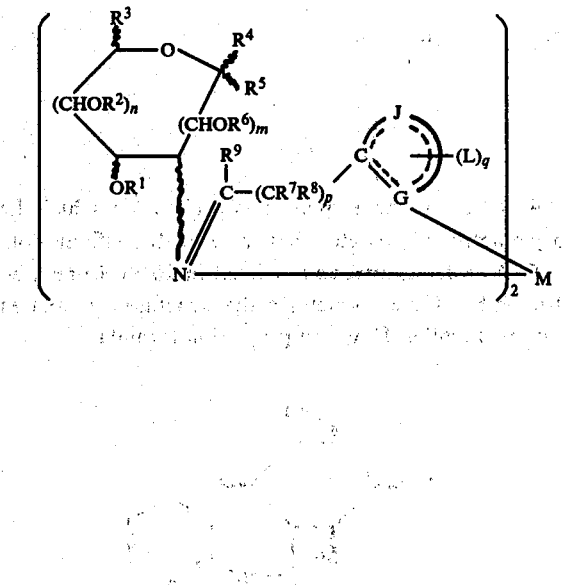

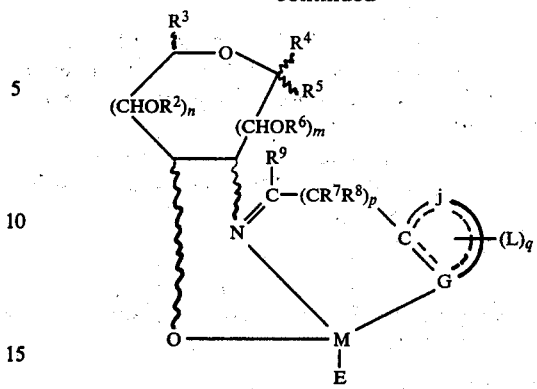

where
R$^{1-9}$, J, L, m, n, p and q have the meanings previously ascribed to them,
E is a monodentate ligand derived from a neutral molecule,
G is nitrogen, =C—O, —N— or =N→O, and
M is a metal from the first or second series of the main group of transition metals.

9. A process for preparing a chiral transition metal complex as claimed in claim 1 which process comprises reacting a chiral Schiff base as defined in claim 12 with a suitable transition metal which is in the form of a salt of an inorganic acid, a complex, or a carboxylate.

* * * * *